(12) United States Patent
Fazio et al.

(10) Patent No.: US 11,752,185 B2
(45) Date of Patent: Sep. 12, 2023

(54) POWDERIZED CANNABIS OIL

(71) Applicant: Hemp Synergistics, Leetsdale, PA (US)

(72) Inventors: Ronald T. Fazio, Beaver Falls, PA (US); Mark A. Mangieri, Oakdale, PA (US); Russell L. Cersosimo, Jr., Gibsonia, PA (US); Gianna H. Fazio, Beaver Falls, PA (US); Daniel P. Kohler, McKees Rocks, PA (US)

(73) Assignee: Hemp Corporation, Crafton, PA (US)

( * ) Notice: Subject to any disclaimer, the term of this patent is extended or adjusted under 35 U.S.C. 154(b) by 69 days.

(21) Appl. No.: 17/333,258

(22) Filed: May 28, 2021

(65) Prior Publication Data

US 2021/0369800 A1 Dec. 2, 2021

Related U.S. Application Data

(60) Provisional application No. 63/031,947, filed on May 29, 2020.

(51) Int. Cl.
*A61K 9/16* (2006.01)
*A61K 36/185* (2006.01)
*A61K 9/50* (2006.01)

(52) U.S. Cl.
CPC .......... *A61K 36/185* (2013.01); *A61K 9/1694* (2013.01); *A61K 9/5036* (2013.01)

(58) Field of Classification Search
None
See application file for complete search history.

(56) References Cited

U.S. PATENT DOCUMENTS

| | | | |
|---|---|---|---|
| 6,197,757 B1 * | 3/2001 | Perrier | B82Y 5/00 514/23 |
| 9,622,982 B2 | 4/2017 | Bannister et al. | |
| 9,629,886 B2 | 4/2017 | Franklin et al. | |
| 10,328,216 B2 | 6/2019 | Boeckl et al. | |
| 10,772,837 B2 | 9/2020 | Lefler et al. | |
| 10,918,120 B2 | 2/2021 | Franklin et al. | |
| 2008/0181942 A1 | 7/2008 | Zajicek | |
| 2012/0231083 A1 | 9/2012 | Carley et al. | |
| 2016/0143972 A1 * | 5/2016 | Stebbins | A61K 36/185 424/725 |
| 2016/0271136 A1 | 9/2016 | Brew et al. | |
| 2017/0252300 A1 | 9/2017 | Modi | |
| 2018/0263953 A1 | 9/2018 | Renwick et al. | |
| 2019/0015383 A1 | 1/2019 | Woelfel et al. | |
| 2019/0133926 A1 | 5/2019 | Jackson | |
| 2019/0192422 A1 | 6/2019 | Shibaz et al. | |
| 2020/0170950 A1 * | 6/2020 | Adair | A61K 31/352 |
| 2020/0316013 A1 | 10/2020 | Karolchyk | |
| 2020/0398184 A1 | 12/2020 | Farokhi et al. | |
| 2021/0030712 A1 | 2/2021 | Peckham et al. | |

FOREIGN PATENT DOCUMENTS

| | | |
|---|---|---|
| CA | 3106476 A1 | 1/2020 |
| CN | 111956641 A | 11/2020 |
| CN | 111150729 B | 2/2021 |
| CN | 112638369 A | 4/2021 |
| JP | 6513576 B2 | 5/2019 |
| WO | 2008139263 A2 | 11/2008 |
| WO | 2018132893 A1 | 7/2018 |
| WO | 2019014631 A1 | 1/2019 |
| WO | 2019219773 A1 | 11/2019 |
| WO | 2020010454 A1 | 1/2020 |
| WO | 2020016658 A3 | 1/2020 |
| WO | 2020018554 A1 | 1/2020 |
| WO | 2020028991 A1 | 2/2020 |
| WO | 2020037410 A1 | 2/2020 |
| WO | 2020180960 A1 | 9/2020 |
| WO | 2020247638 A1 | 12/2020 |
| WO | 2021011928 A1 | 1/2021 |
| WO | 2021028943 A1 | 2/2021 |
| WO | 2021050786 A1 | 3/2021 |

* cited by examiner

*Primary Examiner* — Susan T Tran
(74) *Attorney, Agent, or Firm* — THE WEBB LAW FIRM

(57) ABSTRACT

A method for producing a powderized cannabis oil includes providing a cannabis oil; dissolving the cannabis oil in an alcohol to form a solution; mixing amylose, amylopectin, or a combination thereof into the solution; and evaporating the alcohol.

16 Claims, 4 Drawing Sheets

POWDERIZED CANNABIS OIL

CROSS REFERENCE TO RELATED APPLICATIONS

This application claims priority to U.S. Provisional Patent Application No. 63/031,947, filed May 29, 2020, the disclosure of which is hereby incorporated by reference in its entirety.

BACKGROUND OF THE INVENTION

This present disclosure relates to a pharmaceutical composition that includes a powderized cannabis oil, methods for preparing such compositions, and methods of administering such compositions.

Cannabinoids, such as those found in cannabis plants, known as "hemp" and "marijuana", are commonly used in pharmaceutical compositions. Cannabinoids may be extracted from cannabis plants in the form of oil, referred to as cannabis oil. Alternatively, the term cannabis oil may describe an oil that has been infused with an extracted product or compound from a cannabis plant, such as cannabinoids, flavonoids, terpenes, and/or terpenoids. Other common or industrial names used for oils comprising an extracted product and/or compound of the cannabis plants include cannabis oil, hemp oil, marijuana oil, cannabinoid oil, CBD oil, hemp distillate, RSO, hemp distillate oil, crude, isolate, hemp seed oil, hemp tincture, and marijuana tincture. Cannabis oils are highly viscous substances with elevated adhesion properties to various materials and surfaces used in processing and manufacturing. During processing, residue of the cannabis oil may adhere to components of the manufacturing process, resulting in loss of product. Cannabis oil is insoluble in water and highly resistant to most cleaning agents and detergents, making cleaning of commercial packaging equipment difficult and time consuming. Further, cannabis oil may also adhere to packaging materials used for transporting said cannabis oil, resulting in further product loss.

Cannabis oils are traditionally administered to subjects orally, traveling through the gastrointestinal tract. When the cannabis oil is exposed to acid in the stomach, the cannabis oil will begin to degrade and will not be absorbed effectively into the body, resulting in product loss. In addition, cannabis oil is often delivered pre-mixed in a carrier oil, such as hemp seed oil or MCT oil. Studies have also shown that carrier oils may act as an irritant when introduced in the stomach.

Current technologies used to produce a powderized cannabis oil include simply mixing the cannabis oil, dissolved in a solvent, with polysaccharide(s) or various emulsification techniques. This novel method uses a specific polysaccharide that possesses both hydrophilic and hydrophobic properties, has a three-dimensional structure that can encapsulate other materials, has natural resistance to deleterious effects in processing and ingestion, and is easily digested in the small intestines with normal body enzymes. This novel method also uses heat and atmospheric pressure regulation to increase the encapsulation efficiency to achieve cannabinoid concentrations well above current technologies.

SUMMARY OF THE INVENTION

An object of certain embodiments of the present disclosure is to provide a pharmaceutical composition comprising a powderized cannabis oil.

An object of other embodiments of the present disclosure is to provide a method of preparing a powderized cannabis oil comprising providing a cannabis oil; dissolving the cannabis oil in an alcohol to form a solution; mixing amylose, amylopectin, or a combination thereof into the solution; and evaporating the alcohol to encapsulate the cannabis oil inside of the amylose/amylopectin molecule.

An object of other embodiments of the present disclosure is to provide a method of using atmospheric pressure regulation to increase the efficiency of encapsulation of cannabis oil.

An object of other embodiments of the present disclosure is to provide a method of using a specific class of polysaccharides that possess hydrophilic and hydrophobic properties that facilitate the encapsulation of cannabis oil.

An object of other embodiments of the present disclosure is to provide a method of using a specific class of polysaccharides that possess specific glycosidic bonds that are easily broken by natural digestion enzymes found in the small intestines but have resistance to deleterious effects in handling, processing, and in the mouth, esophagus, and stomach.

An object of certain embodiments of the present disclosure is to provide a method of administering a pharmaceutical composition for targeting the endocannabinoid system, comprising administering a pharmaceutical composition comprising a powderized cannabis oil.

Examples of the present invention will now be described in the following numbered clauses:

Clause 1: A method for preparing a powderized cannabis oil, comprising: a) providing a cannabis oil; b) dissolving the cannabis oil in an alcohol to form a solution; c) mixing amylose, amylopectin, or a combination thereof into the solution; and d) evaporating off the alcohol.

Clause 2: The method of clause 1, wherein the alcohol is evaporated at room temperature.

Clause 3: The method of clause 1, wherein the alcohol is evaporated at a temperature in the range of 20° C. to 100° C.

Clause 4: The method of any of clauses 1-3, wherein the evaporating step further comprises removing the alcohol with a vacuum at a pressure within the range of 0 mmHg to 760 mmHg.

Clause 5: The method of any of clauses 1-4, further comprising mixing the amylose, amylopectin, or a combination thereof into the solution at a temperature within the range of 20° C. to 100° C.

Clause 6: The method of any of clauses 1-5, wherein the mixing step further comprising agitating the solution.

Clause 7: The method of any of clauses 1-6, wherein the alcohol comprises methanol, ethanol, propanol, butanol, pentanol, hexanol, heptanol, or a combination thereof.

Clause 8: The method of any of clauses 1-7, wherein the powderized cannabis oil further comprises flow agents, vitamin or nutritional components, stabilizing, preservative, or anti-oxidative additives, or a combination thereof.

Clause 9: A method of administering a pharmaceutical composition for targeting the endocannabinoid system, comprising administering a pharmaceutical composition comprising a powderized cannabis oil.

Clause 10: The method of clause 9, wherein the pharmaceutical composition is free of carrier oils that cause stomach irritation.

Clause 11: The method of any of clauses 9-10, wherein the pharmaceutical composition comprising the powderized cannabis oil is administered together with a cannabinoid containing composition.

Clause 12: The method of any of clauses 9-11, wherein the pharmaceutical composition is in a form of tablets or capsules for oral administration.

Clause 13: The method of any clauses 9-11, wherein the pharmaceutical composition is in the form of a functional food or beverage for oral administration.

Clause 14: A powderized cannabis oil comprising a cannabis oil at least partially encapsulated by amylose, amylopectin, or a combination thereof.

Clause 15: The powderized cannabis oil of clause 14, wherein a weight ratio of cannabis oil to amylose, amylopectin, or a combination thereof is within a range of from 1:1000 to 3:2, respectively.

Clause 16: A pharmaceutical composition comprising the powderized cannabis oil of any of clauses 14-15.

DESCRIPTION OF THE INVENTION

Figure 1:
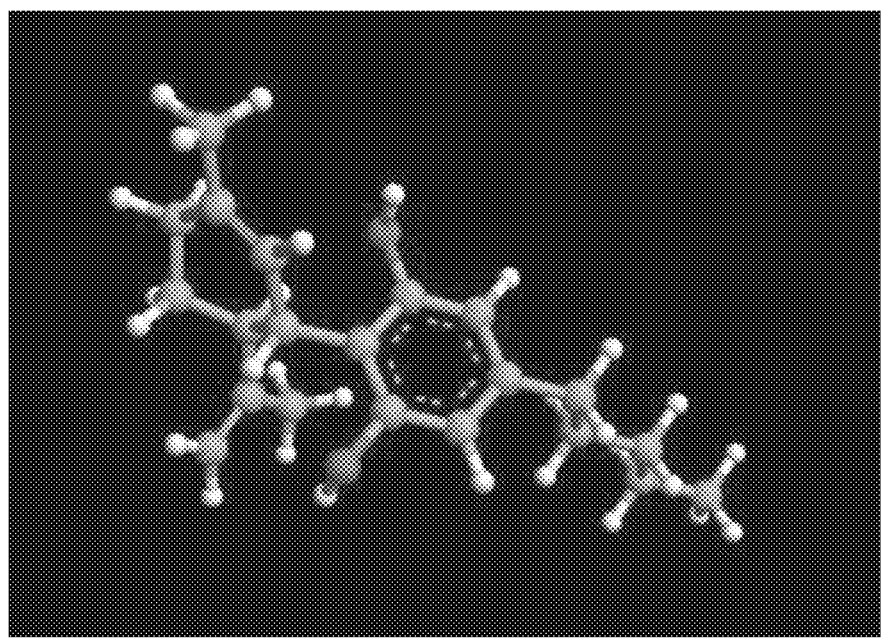
FIG. 1 shows an image of a three-dimensional rendering of a cannabidiol (CBD) molecule.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. As used in the specification and the claims, the singular form of "a", "an", and "the" include plural referents unless the context clearly dictates otherwise.

For purposes of the following detailed description, it is to be understood that the invention may assume various alternative variations and step sequences, except where expressly specified to the contrary. Moreover, other than in any operating examples, or where otherwise indicated, all numbers expressing, for example, quantities of ingredients used in the specification and claims are to be understood as being modified in all instances by the term "about". Accordingly, unless indicated to the contrary, the numerical parameters set forth in the following specification and attached claims are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10.

A non-limiting embodiment of the present invention relates to a method for producing a powderized cannabis oil. The method may include providing a cannabis oil; dissolving the cannabis oil in an alcohol to form a solution; mixing amylose, amylopectin, or a combination thereof into the solution; optionally controlling and regulating the ambient pressure; and evaporating the alcohol.

Cannabinoids may be removed from cannabis plants in the form of an oil. For example, cannabinoids may be removed from the cannabis plant using critical fluid carbon dioxide ($CO_2$), hydrocarbon, alcohol, and/or super-chilled alcohol extraction methods. The cannabis oil extracted from said plants is highly viscous with increased adhesion properties. During processing, the cannabis oil may adhere to various surfaces and materials used in processing. Specifically, viscous cannabis oil causes processing complications for machines such as capsule packaging or filling machines, which will delay manufacturing time, drastically increase difficulty for cleaning equipment, result in product loss, and make exact dosing difficult. By encapsulating the cannabis oil in amylose and/or amylopectin to form a powderized cannabis oil, a powderized cannabis oil is formed with lower adhesion such that it does not adhere to manufacturing surfaces. As used herein, "encapsulating" refers to at least partially, or entirely, enclosing the cannabis oil within the amylose and/or amylopectin, such as enclosed in and among the helix structures of specific polymeric chains of the amylose and/or amylopectin.

The cannabis oil is a naturally occurring, biological product and therefore there is inherent variability in the specific components that comprise the cannabis oil. In general, the cannabis oil can comprise proteins, fats, aliphatic and/or aromatic compounds, fatty acids, such as omega-3 and omega-6 fatty acids and γ-linolenic acid. For example, the cannabis oil may comprise fatty acids such as γ-linolenic acid, stearidonic acid, oleic acid, eicosenoic acid, and other saturated fatty acids, such as palmitic and stearic acids. Additional components of the cannabis oil may include terpenes, terpenoids, Vitamin E, phytosterols, phospholipids, chlorophyll, carotenes, and minerals.

The cannabis oil may comprise one or several naturally occurring cannabinoids, and acid derivatives thereof. Non-limiting examples of naturally occurring cannabinoid compounds include cannabigerol (CBG), Δ9-tetrahydrocannabinol (THC), cannabidiol (CBD), cannabichromene (CBC), cannabigerivarin (CBGV), tetrahydrocannabivarin (THCV), cannabidivarin (CBDV), cannabichromevarin (CBCV), and the like. Cannabis oil has inherent variability in the specific concentrations of cannabinoids. A three-dimensional rendering of one such molecule, cannabidiol (CBD), is shown in FIG. 1. The cannabis oil may also comprise man-made or synthetic cannabinoids. Cannabis oil is susceptible to oxidation and therefore may also comprise antioxidants including, but not limited to, tocopherols and ascorbic acid to inhibit oxidation.

The cannabis oil may comprise a carrier oil. As used herein, a "carrier oil" is any food grade oil that can incorporate a cannabinoid compound, such as a food grade oil that can incorporate a cannabis oil. If a carrier oil is present, the carrier oil, as well as the cannabis oil and/or cannabinoid containing compound, may be encapsulated by amylose and/or amylopectin such that the carrier oil and/or cannabis oil may not substantially degrade, or degrade in any amount, in the stomach, preventing stomach irritation. Alternatively, the cannabis oil, and the powderized cannabis oil disclosed herein, may be free of a carrier oil.

The powderized cannabis oil may be formed according to the process as follows. The cannabis oil may be dissolved in an alcohol. Any alcohol known in the art may be used to dissolve the cannabis oil. For example, a water miscible alcohol can be used to dissolve the cannabis oil. Non-limiting examples of suitable alcohols for dissolving the cannabis oil include methanol, ethanol, propanol, butanol, pentanol, hexanol, heptanol, and combinations thereof.

After the cannabis oil has been substantially dissolved in the alcohol, amylose and/or amylopectin may be added to the solution and mixed. For example, the dissolution level of the cannabis oil in the alcohol may be such that the amylose and/or amylopectin may be added to form a homogenous mixture. For instance, the cannabis oil and alcohol may be present in a ratio of 1:1, based on the weight (in grams) of the cannabis oil and the volume (in milliliters) of the alcohol. The cannabis oil and the amylose and/or amylopectin may be added, gravimetrically or volumetrically, in specific and desired quantities such that a final product is produced with a specific concentration of cannabis oil, amylose and/or amylopectin, or specific cannabinoid that is consistent from batch to batch. For example, the ratio of cannabis oil to amylose and/or amylopectin, in terms of weight percentage, may be at least 1:1000, respectively. The ratio of cannabis oil to amylose and/or amylopectin, in terms of weight percentage, may be up to 2:3, or may be up to 3:2, respectively. The cannabis oil can be added in various amounts, such that various doses can be achieved with the same amount of powder. Amylose and amylopectin are polysaccharides made of α-D-glucose units, bonded to each other through 1,4-glycosidic bonds that form molecular helix structures.

Figure 2:
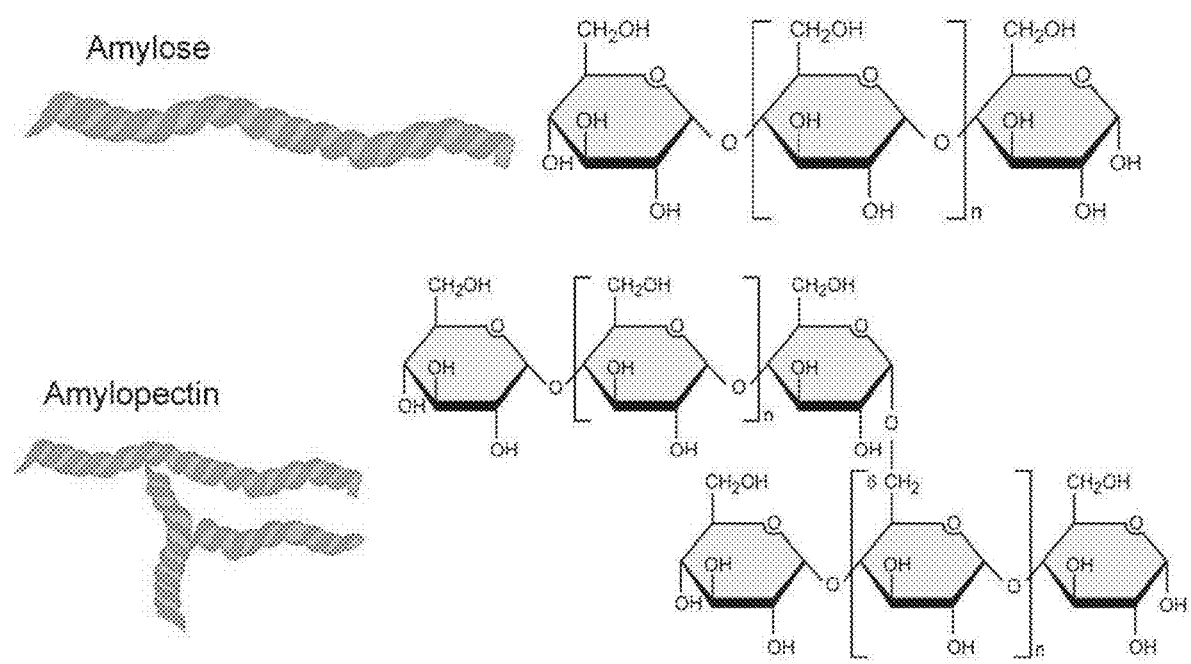
FIG. 2 shows an image of the molecular structures of amylose and amylopectin.

Amylose is a linear polysaccharide comprised, generally, of greater than 300 repeat units of glucose molecules that are bonded to each other with alpha 1,4-glycosidic bonds. Amylopectin is a highly branched polysaccharide. The linear portion of amylopectin is similar to that of amylose in that the linear portion of amylopectin comprises repeat units of glucose molecules bonded together with alpha 1,4-glycosidic bonds. Branch units of glucose molecules occur in amylopectin approximately from 24-30 main chain glucose repeat units and the branch units of glucose are bonded to the linear main chain with alpha 1,6-glycosidic bonds. An image of the molecular structures of both amylose and amylopectin is shown in FIG. 2. The nature of the alpha 1,4-glycosidic bonds allow for the linear main chains of amylose and amylopectin to assume a bent orientation that forms a hollow helix structure. This hollow helix structure is suitable for excellent energy access and storage applications. Amylopectin is relatively insoluble in both oil and water, while amylose is relatively insoluble in oil, making the use of amylose and amylopectin to encapsulate the cannabis oil very difficult. However, when alcohol is used as the solvent, amylose and amylopectin may be readily incorporated into the solution. Non-limiting examples of suitable alcohols, with the corresponding chemical formulas, are shown in Table 1 below.

TABLE 1

| Solvent | Chemical Formula |
| --- | --- |
| Methanol | $CH_3OH$ |
| Ethanol | $C_2H_5OH$ |
| Propanol | $C_3H_7OH$ |
| Butanol | $C_4H_9OH$ |
| Pentanol | $C_5H_{11}OH$ |
| Hexanol | $C_6H_{13}OH$ |
| Heptanol | $C_7H_{15}OH$ |

The 1,4-glycosidic bonds in amylose and amylopectin are resistant to normal oxidation and mild acidic environments, such as in the stomach. Although these bonds are chemically resistant and stable, they are easily broken by amylase and isomaltase, natural enzymes found in abundance in the small intestine. Cannabinoids and oils are predominately absorbed in the small intestines.

The three-dimensional helical structure of amylose and amylopectin has a hydrophobic interior that preferentially bind with hydrophobic molecules, including lipids and cannabinoids.

Heating of the amylose and amylopectin while incorporated with the cannabis oil and alcohol relaxes the three-dimensional structure, facilitating the encapsulation of the cannabis oil and cannabinoids.

Once the amylose and/or amylopectin is added to the solution of cannabis oil dissolved in the alcohol, the components are thoroughly mixed until the amylose and/or amylopectin is thoroughly incorporated. In order to aid in the incorporation of the amylose and/or amylopectin, the solution containing the cannabis oil, alcohol, and amylose and/or amylopectin may be heated. The solution may be heated to a temperature in the range of 20° C. to 100° C., such as room temperature (i.e., 20° C. to 25° C.), up to or near the boiling temperature of the alcohol used. For example, ethanol ($C_2H_5OH$), has a boiling temperature (at standard atmospheric pressure) of 78.37° C. Vacuum may be applied to lower the required temperature.

A method of agitating may be applied to the solution in order to aid in the incorporation of the amylose and/or amylopectin. Non-limiting examples of suitable agitating methods include ultrasonic, mechanical, and centrifugal. Ultrasonic agitating may be performed using a sonicator which uses sound energy at an ultrasonic frequency to agitate the particles in the solution. Mechanical agitating may be performed using common laboratory techniques such as rotational mixing and stirring using a stirring rod and/or stone. Centrifugal agitating may be performed using a centrifuge that rotates the solution at high speeds, applying a centrifugal force to the solution.

Figure 3:
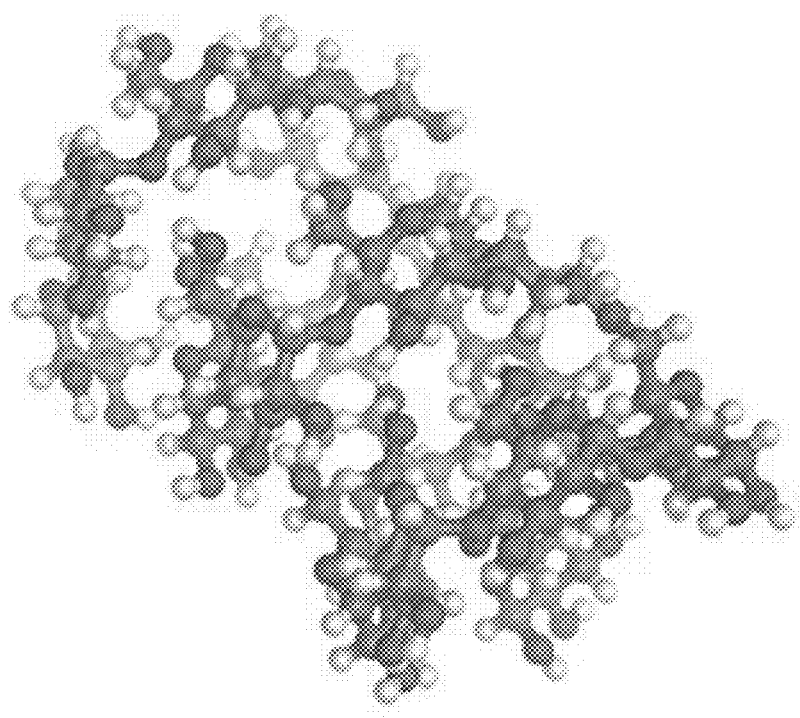
FIG. 3 shows an image of a three-dimensional rendering of multiple amylose polymer chains suitable for encapsulating cannabis oil.

Upon adequate incorporation of the amylose and/or amylopectin into the solution, the cannabis oil is introduced into the helix and structure such that the cannabis oil is encapsulated by the amylose and/or amylopectin. The cannabis oil may be encapsulated in and/or among a group or bundle of various polymeric chains of different amylose and/or amylopectin molecules, such that multiple molecules amylose and/or amylopectin are used to encapsulate a certain portion of the cannabis oil. In FIG. 3, a three-dimensional rendering of multiple polymeric chains of amylose is shown. The cannabis oil moves within the structure of the multiple polymeric chains in the solution and becomes trapped within the polymeric chains, which successfully encapsulates the cannabis oil within the multiple polymeric chains of the amylose. After the incorporation of the amylose and/or amylopectin into the solution, the alcohol may be removed through evaporation. To aid in the removal of the alcohol, the solution may be heated. The solution may be heated to a temperature above room temperature (20-25° C.), but not to exceed the retrogradation temperature of the amylose (about 150° C.) or amylopectin (about 50-60° C.). As used herein, the "retrogradation temperature" is the temperature at which, when exceeded, the crystalline structure of a polysaccharide begins to breakdown.

The atmospheric pressure is lowered, typically with a vacuum chamber, to not only further assist in the removal of the alcohol, but primarily to facilitate the encapsulation of the cannabis oil and cannabinoids within the three-dimensional helical structure of the amylose/amylopectin. The atmospheric pressure may be cycled from low to ambient pressure repeatedly to maintain or improve the encapsulation process. The pressure may be cycled in the range of 0 mmHg to about 760 mmHg, or ambient pressure. In order to ensure that all of the cannabis oil is fully introduced into the helix structure of the amylose and amylopectin, the evaporation/removal rate of the alcohol may be controlled. For instances, the evaporation/removal rate of the alcohol may be controlled such that the evaporation/removal rate does not exceed the absorption ability of the cannabis oil by the amylose and/or amylopectin to allow for sufficient encapsulation of the cannabis oil by the amylose and/or amylopectin. The evaporation/removal rate of the alcohol may be controlled such that the alcohol remaining in the solution does not exceed toxicology/nutritional regulatory limits. For example, the time it takes for the alcohol to be evaporated may be at least 1 hour. The pressure may be cycled numerous times to facilitate the absorption and encapsulation of the cannabis oil.

Additional components may be added to the solution in order to aid in the absorption and encapsulation of the cannabis oil into the helix structure of the amylose and/or amylopectin, and/or to produce a final powderized cannabis oil with specific properties. Non-limiting examples of suitable additional components include flow agents such as colloidal silicon dioxide, magnesium stearate and stearic acid, vitamin or nutritional components such as Vitamin C, Vitamin D, Vitamin E, minerals, and the like, and stabilizing, preservative, or anti-oxidative additives such as tocopherols, ascorbic acid, and the like. These additional components may be added at any time during the production of the powderized cannabis oil, such as during the alcohol mixing step, or may be added and mixed with the final powderized cannabis oil.

Once all of the alcohol is evaporated, the resulting final product is an all-natural (e.g., vegan), dry, non-oily powderized cannabis oil that comprises the cannabis oil encapsulated in the amylose and/or amylopectin. The powderized cannabis oil has low adhesion such that only a small amount or no residue is left on packaging materials and containers or manufacturing surfaces. The low adhesion also allows for the powderized cannabis oil to be easily measured and handled for use in pharmaceutical compositions with exact dosages without product loss. The powderized cannabis oil also has low electrostatic properties and can easily be packed into high densities at specific concentrations for dosage measuring and transportation purposes.

The powderized cannabis oil has little to no odor or taste, facilitating its use in foods, beverages, and nutraceuticals.

A pharmaceutical composition comprising the powderized cannabis oil is also disclosed herein. The pharmaceutical composition can be formulated into several fixed-dosage forms, including but not limited to, solid fixed-dosage forms for oral administration such as capsules, tablets, pills, powders, and granules. The pharmaceutical composition comprising the powderized cannabis oil may be used to target the endocannabinoid system of a subject, such as a cannabinoid receptor found in the endocannabinoid system. The powderized cannabis oil is provided in an effective amount for targeting the endocannabinoid system, such as to target aspects of the endocannabinoid system associated with one or more conditions. For example, the pharmaceutical composition comprising the powderized cannabis oil may be administered to a subject experiencing one or more conditions, such as conditions associated with the endocannabinoid system. For example, the pharmaceutical composition may be administered to a subject experiencing inflammation, anxiety disorders, and/or one or more additional conditions associated with the endocannabinoid system. For instance, EPIDIOLEX, a prescription medicine of the cannabinoid Cannabidiol (CBD), is used to treat seizures associated with Lennox-Gastaut syndrome or Dravet syndrome. In clinical studies, CBD was shown to have a therapeutic dose at 10 mg/kg/day. A 100-pound (68 kg) person would require an approximate 680 mg daily dose to reach the therapeutic dose. This invention can deliver 680 mg of CBD in as little as two capsules with little need for compaction.

For example, a "00" capsule (commonly used size capsule) can hold approximately 0.95 milliliters of product. This invention of powderized cannabis oil can easily compact to 0.80 grams per milliliter. Therefore, the powderized cannabis oil may be delivered in amounts up to (or exceeding) 760 mg per 00 capsule. Considering that concentrations of cannabinoids in cannabis oil can reach 95% and the powderized cannabis oil is 54% cannabis oil, the 00 capsule can easily hold over 390 mg of cannabinoids. The preferred amount of powderized cannabis oil delivered to each capsule would depend on the dosing amount, inclusion of other active ingredients, and size of capsule. This invention can completely customize the amount of cannabis oil and cannabinoid dosing target.

Figure 4:
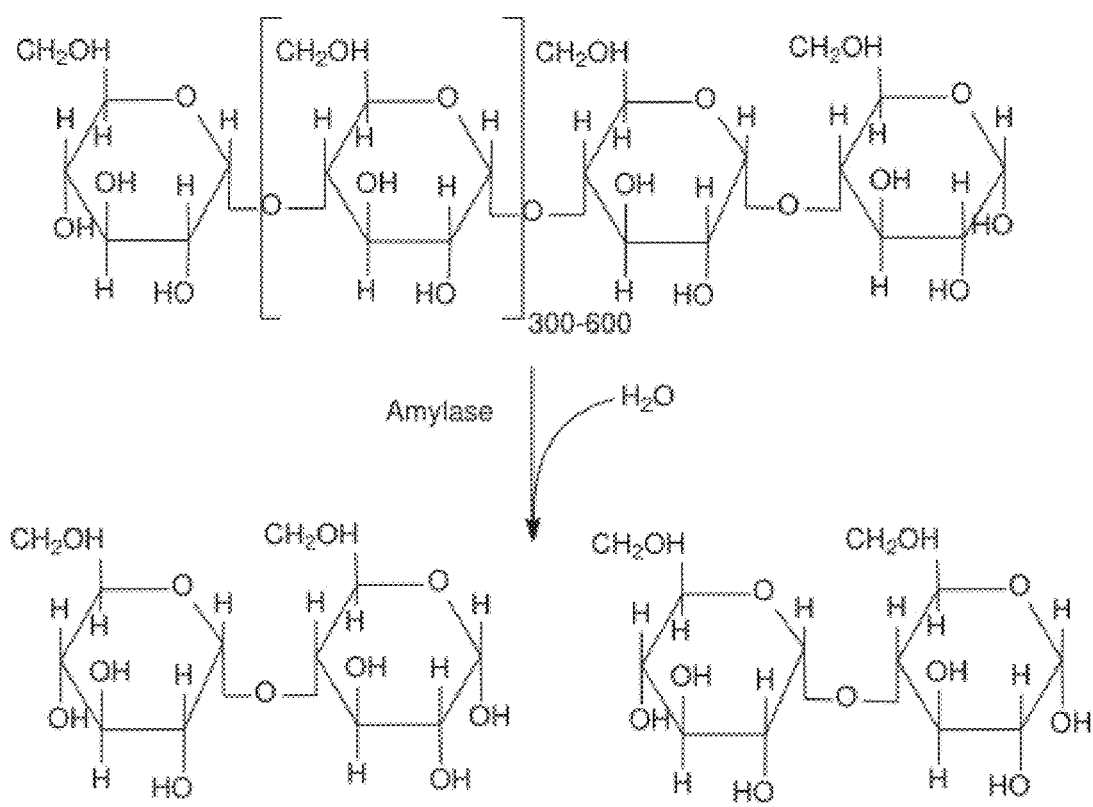
FIG. 4 shows a schematic of how amylase enzymes break down amylose.

The pharmaceutical composition comprising the powderized cannabis oil eliminates the need for a carrier oil, reducing the chance for irritation in the stomach. In addition, the powderized cannabis oil is protected by the polysaccharides, reducing the opportunity for the oil or cannabinoids to undergo deleterious degradation in the stomach. The powderized cannabis oil then passes into the small intestine where natural enzymes such as amylase and isomaltase break down the amylose and/or amylopectin, releasing the cannabis oil. FIG. 4 shows the mechanism of how amylose/amylopectin chains are broken down by amylase, such as the amylase present in the small intestines. The released cannabis oil is then emulsified and absorbed by natural biological processes.

The pharmaceutical composition comprising of powderized cannabis oil allows for the standardization of concentration of a target cannabinoid or cannabinoids, facilitating large scale production of capsules, foods, or beverages.

The pharmaceutical composition comprising of powderized cannabis oil can be easily incorporated into foods and beverages without adding taste or odor to the final product.

The pharmaceutical composition can include purified amylose, improving water solubility/suspend-ability of the powderized cannabis oil.

The following prophetic example is presented to demonstrate the general principles of the invention of this disclosure. The invention should not be considered as limited to the specific examples presented. All parts and percentages in the examples are percent weight, based on the total weight of the pharmaceutical composition, unless otherwise indicated.

EXAMPLE

An amount of 4 grams of cannabis oil was measured out and added to a beaker containing 4 mL of ethanol. The cannabis oil and ethanol were stirred and agitated until the cannabis oil was fully dissolved. An amount of 6 grams of amylose and/or amylopectin, obtained from tapioca flour, was added to the beaker and was stirred until all components were thoroughly mixed. The beaker was then removed from the heat and stirring continued until the mixture became creamy and consistent. The mixture was allowed to rest for 30 minutes, then placed in a vacuum at 300 mmHg for 15 minutes. After 15 minutes, the vacuum was released and re-applied. The process of applying vacuum and releasing was repeated three times. The mixture was then removed from the vacuum and stirred to remove any remaining clumps and allowed to rest for 12 hours. After the 12 hour rest, the material was ground and sieved through a 50 mesh screen, then packaged in an air-tight container. The final product included 10 grams of powderized cannabis oil with a 40% cannabis oil concentration. The final powderized cannabis oil has an amber color, is powdery, and easily compactable. The odor of the powderized cannabis oil is minimal and the taste is initially flavorless until the amylose and/or amylopectin is broken down by the amylase in saliva, at which point the powderized cannabis oil has the taste of cannabinoids and cannabis oil. The powderized cannabis oil is not readily dissolved in neutral or acidic mediums and does not leave residue on packaging containers. The powderized cannabis oil is compressible to 800 milligrams per milliliter, allowing for up to 760 milligrams per 00 capsule, for a total of 304 milligrams of cannabis oil per capsule.

It is to be understood that the invention may assume various alternative variations, except where expressly specified to the contrary. It is also to be understood that the specific devices illustrated in the attached drawings, and described in the specification, are simply exemplary embodiments of the invention. Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope thereof. For example, it is to be understood that the present invention contemplates that, to the extent possible, one or more features of any embodiment can be combined with one or more features of any other embodiment. The embodiments of the invention described herein above in the context of the preferred embodiments are not to be taken as limiting the embodiments of the invention to all of the provided details thereof, since modifications and variations thereof may be made without departing from the spirit and scope of the embodiments of the invention.

The invention claimed is:

1. A method for preparing a powderized cannabis oil, comprising:
    a) providing a cannabis oil;
    b) dissolving the cannabis oil in an alcohol to form a solution;
    c) mixing amylose, amylopectin, or a combination thereof into the solution, thereby enclosing the cannabis oil in and among the helix structures of the amylose, amylopectin, or combinations thereof; and
    d) evaporating off the alcohol.

2. The method of claim 1, wherein the alcohol is evaporated at room temperature.

3. The method of claim 1, wherein the alcohol is evaporated at a temperature in the range of 20° C. to 100° C.

4. The method of claim 1, wherein the evaporating step further comprises removing the alcohol and improving the absorption and encapsulation with a vacuum at a pressure within the range of 0 mmHg to 760 mmHg.

5. The method of claim 1, further comprising mixing the amylose, amylopectin, or a combination thereof into the solution at a temperature within the range of 20° C. to 100° C.

6. The method of claim 1, wherein the mixing step further comprising agitating the solution.

7. The method of claim 1, wherein the alcohol comprises methanol, ethanol, propanol, butanol, pentanol, hexanol, heptanol, or a combination thereof.

8. The method of claim 1, wherein the mixture further comprises flow agents, additives, or a combination thereof.

9. A method of administering a pharmaceutical composition for targeting the endocannabinoid system, comprising administering a pharmaceutical composition comprising a powderized cannabis oil prepared according to the method of claim 1.

10. The method of claim 9, wherein the pharmaceutical composition is free of carrier oils that cause stomach irritation.

11. The method of claim 9, wherein the pharmaceutical composition comprising the powderized cannabis oil is administered together with a cannabinoid containing composition.

12. The method of claim 9, wherein the pharmaceutical composition is in a form of tablets or capsules for oral administration.

13. The method of claim 9, wherein the pharmaceutical composition is in the form of a functional food or beverage for oral administration.

14. A powderized cannabis oil prepared according to the method of claim 1.

15. The powderized cannabis oil of claim 14, wherein a weight ratio of cannabis oil to amylose, amylopectin, or a combination thereof is within a range of from 1:1000 to 3:2, respectively.

16. A pharmaceutical composition comprising the powderized cannabis oil of claim 14.

* * * * *